United States Patent [19]

Engelhart et al.

[11] 4,130,411

[45] Dec. 19, 1978

[54] COMPOSITIONS FOR REGULATING UNDESIRABLE PLANT GROWTH

[75] Inventors: John E. Engelhart, Westfield; Maynard W. McNeil, Washington, both of N.J.

[73] Assignee: M&T Chemicals Inc., Stamford, Conn.

[21] Appl. No.: 739,117

[22] Filed: Nov. 5, 1976

[51] Int. Cl.$^2$ .......................... A01N 9/36; A01N 5/00
[52] U.S. Cl. ............................................. 71/86; 71/87; 71/76; 71/71; 71/72
[58] Field of Search ............................... 71/86, 87, 76

[56] References Cited

U.S. PATENT DOCUMENTS

| | | | |
|---|---|---|---|
| 2,714,064 | 7/1955 | Morris et al. | 71/86 |
| 2,927,014 | 3/1960 | Goyette | 71/86 |
| 3,158,461 | 11/1964 | Weil | 71/86 |
| 3,248,459 | 4/1966 | Lorenz | 71/86 X |

OTHER PUBLICATIONS

Zhurnal Obshchei Kimii, vol. 28 (1958).

*Primary Examiner*—Catherine L. Mills
*Attorney, Agent, or Firm*—Kenneth G. Wheeless; Robert Spector

[57] ABSTRACT

Tertiary phosphine oxides containing two halomethyl radicals effectively control the growth of undesirable plants, particularly grasses.

10 Claims, No Drawings

COMPOSITIONS FOR REGULATING UNDESIRABLE PLANT GROWTH

This invention relates to phytotoxic compositions. This invention further relates to compositions containing certain organophosphorus compounds that effectively kill or regulate the growth of undesirable plants, particularly grasses such as millet and crabgrass.

Several phosphine oxides containing two chloromethyl groups and a substituted phenyl group are reported in the chemical literature, for example in Zhurnal Obshchei Kimii 28, 2853 (1958). To our knowledge there has been no disclosure of biological activity for the corresponding bromo- and iodomethyl compounds.

SUMMARY OF THE INVENTION

This invention provides compositions for controlling the growth of undesirable plants, said compositions consisting essentially of at least one inert carrier and an amount of an organophosphorus compound $$(XCH_2)_2PR$$
$$\overset{O}{\|}$$

sufficient to kill or regulate the growth of said plants, wherein X is bromine or iodine and R is selected from the growth consisting of

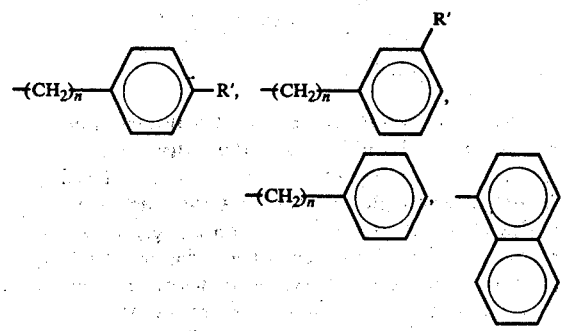

haloalkyl and alkyl wherein the halogen is chlorine, bromine or iodine and the alkyl residue contains from 1 to 20 carbon atoms, $-NR''_2$, $-OR''$ and $-SR''$, R' is, in turn, selected from the group consisting of $CF_3$, $CCl_3$, fluorine, chlorine, bromine, iodine, linear alkyl containing from 1 to 20 carbon atoms and linear alkoxy containing from 1 to 20 carbon atoms, R'' being selected from the group consisting of unsubstituted and substituted alkyl containing from 1 to 20 carbon atoms, alkenyl and aryl and n is 0 or 1.

DETAILED DESCRIPTION OF THE INVENTION

The present organophosphorus compounds are capable of modifying the development and growth of many undesirable plants, particularly grasses. These modifications include all deviations from natural development, such as killing, growth retardation, defoliating and stunting. The compounds can be applied before or after emergence of the plant, however the compounds are usually most effective as pre-emergence herbicides against various types of grasses, including foxtail millet, Japanese millet and crabgrass.

When R and R'' in the preceding formula represent alkyl or alkenyl, these groups can be substituted with one or more substituents such as halogen or alkoxy.

Bis(chloromethyl)phenylphosphine oxides wherein the phenyl ring contains one or more alkyl, halogen or dimethylamino groups are conveniently prepared by reacting the corresponding arylmagnesium halide with bis(chloromethyl)phosphinic chloride, $$(ClCH_2)_2PCl.$$
$$\overset{O}{\|}$$

Bis(bromomethyl)- and bis(iodomethyl)phenylphosphine oxides can be obtained from the corresponding bis(chloromethyl) compound by reacting it with an alkali metal bromide or iodide. Lithium bromide and sodium iodide are preferred due to their solubility in the reaction media.

Some typical preparative methods are set forth in the following examples.

EXAMPLE 1

Preparation of bis(chloromethyl)phenylphosphine oxide.

A three-necked reaction vessel equipped with a reflux condenser, mechanically driven stirrer, nitrogen inlet and thermometer was charged with 91 g. of bis(chloromethyl)phosphinic chloride and 150 cc. tetrahydrofuran. A 280 g. portion of a tetrahydrofuran solution containing 2.0 moles of phenylmagnesium chloride per kilogram of solution was gradually added to the reaction mixture at a rate such that the temperature of the reaction mixture did not exceed 30° C. The resultant mixture was stirred for one hour following completion of the addition, at which time an excess of water was added and the organic phase isolated. The aqueous phase was extracted once with chloroform and the chloroform layer combined with the previously isolated organic layer. The organic solvents were then evaporated under reduced pressure to yield an offwhite solid which was slurried with a small amount of diethyl ether and filtered. The isolated solid material weighed 62.0 g. and melted from 135° to 137° C. The reported melting range for the compound is 141°–142° C.

EXAMPLE 2

Preparation of bis(iodomethyl)phenylphosphine oxide

The product of Example 1 (20 g.) was combined with 50 g. of sodium iodide and 400 cc. of acetone, and then heated to the boiling point for a total of 9 hours and 45 minutes. The solid sodium chloride was filtered off and the acetone evaporated under reduced pressure. The resultant solid was slurried in 200 cc. water, isolated, slurried in acetone and finally isolated again by filtering. The recovered solid was recrystallized using ethanol to yield 12 g. of white solid that melted from 175° to 177° C. The reported melting range for the compound is 172°–173° C. Evaporation of the ethanol yielded an additional 3 g. of solid material.

EXAMPLE 3

Preparation of bis(iodomethyl)-p-tolylphosphine oxide

The title compound was obtained using the procedure of the preceding two examples, with the exception that p-tolylmagnesium bromide was used in place of phenylmagnesium bromide. The p-tolylmagnesium bromide was prepared using 8.6 g. (0.05 mole) p-bromotoluene, 1.5 g. magnesium and 60 cc. tetrahydrofuran and was reacted with 9 g. (0.05 mole) of bis(chloromethyl)-phosphinic chloride dissolved in 100 cc. of diethyl ether. The product from this reaction was heated for about 16 hours with 15 g. of sodium iodide dissolved in 75 cc. of 2-butanone. The solid obtained following removal of the solvent was combined with a solution containing 1 g. of sodium bisulfite and 100 cc. water. The solid phase was then isolated and recrystallized from acetone to yield 6 g. of a solid melting from 155° to 160° C. Upon analysis the solid was found to contain 60.18% by weight of iodine, 7.39% by weight of phosphorus, 26.05% carbon and 2.85% hydrogen. The calculated values for bis(iodomethyl)-p-tolylphosphine oxide are 60.43%, 7.38%, 25.74% and 2.64%, respectively.

EXAMPLE 4

Preparation of bis(bromomethyl)-p-chlorophenylphosphine oxide

The title compound was prepared using a procedure similar to that outlined in the preceding Example 3. The intermediate product, bis(chloromethyl)-p-chlorophenylphosphine oxide was obtained by reacting 101.5 g. of bis(chloromethyl) phosphinic chloride with p-chlorophenylmagnesium bromide (450 g. of a 1.25 molal solution in tetrahydrofuran) using the procedure described in the preceding Example 1. Isolation of the intermediate product was effected by combining the reaction mixture with 200 cc. of water and 25 cc. concentrated hydrochloric acid. The organic layer was then isolated and most of the tetrahydrofuran was evaporated under reduced pressure. The p-bromochlorobenzene formed as a by-product during the reaction was removed by steam distillation. The solid residue in the reaction vessel was dissolved in hot chloroform and the resultant solution filtered to remove suspended material. A solid material precipitated as the solution cooled and was removed by filtration. A second portion of solid weighing 47 g. precipitated from the filtrate and melted from 152° to 154° C. The reported melting point for bis(chloromethyl)-p-chlorophenylphosphine oxide is 150°–151° C. This product (4 g.) was subsequently combined with 10 g. of lithium bromide and 50 cc. 2-butanone and heated at the boiling point for about 16 hours. The 2-butanone was then evaporated under reduced pressure and replaced by a mixture containing 50 cc. water and 30 cc. chloroform. Two grams of undissolved solids, melting at 179°–180° C., were removed by filtration. Upon analysis the solid was found to contain 66.87% by weight of bromine. The value calculated for the title compound is 66.15%. Another 3 g. of solids were obtained by isolating the organic phase and evaporating the solvent under reduced pressure. The material melted from 173° to 174° C.

Procedures similar to those described in the preceding four examples were employed to prepare all of the compounds evaluated as herbicides. The following table summarizes the organomagnesium compound and any reagents other than the phosphorus compound employed. In all instances the phosphorus compound was bis(chloromethyl)phosphinic chloride. If the final product contained a bromine or iodine atom on the methyl group, the substitution was accomplished using lithium bromide or sodium iodide.

| X | R | Reagents [other than $(ClCH_2)_2\overset{O}{\underset{\|}{P}}Cl$] |
|---|---|---|
| Br | –C₆H₄–Cl | BrMg–C₆H₄–Cl, LiBr |
| Br | –C₆H₄–F | BrMg–C₆H₄–F, LiBr |
| I | –C₆H₄–C₆H₅ | BrMg–C₆H₄–C₆H₅, NaI |
| I | –C₆H₄–OCH₃ | BrMg–C₆H₄–OCH₃, NaI |
| I | –C₆H₄–Cl | BrMg–C₆H₄–Cl, NaI |
| I | CH₂–C₆H₅ | BrMgCH₂–C₆H₅, NaI |

An organomagnesium compound was not employed to prepare those phosphinic acid derivatives wherein R represents $-N(CH_2CH=CH_2)_2$ or $-S-CH(CH_8)_2$. The diallyl amine derivative was prepared by reacting bis(chloromethyl)phosphinic chloride (9 g.) with diallyl amine (10 g.) in the presence of triethylamine (6 g.) as an acid acceptor. The resultant product was reacted with sodium iodide. The sulfur-containing compound was prepared in a similar manner by substituting isopropyl mercaptide for the diallyl amine.

Representative compounds were evaluated as pre-emergence and post-emergence herbicides for grasses and broadleaf weeds. An area of topsoil containing seeds was sprayed with 50 cc. of a solution or dispersion of the test chemical. The solution or dispersion had previously been prepared by dissolving or dispersing the test compound in acetone, adding an anionic surfactant (Triton ® X-155, manufactured by Rohm & Haas) and then diluting with water such that the final product contains 5–10% acetone, 100 p.p.m. surfactant and 2080 p.p.m. of the test chemical. The total area of soil treated was one square foot. The post-emergence test was conducted by spraying mature plants using 50 cc. of the same formulation used in the pre-emergence test. The plants were on trays having a surface area of one square foot that was completely covered with soil.

The seeds for both the pre- and post-emergence tests are placed in furrows about ¼ to ½ inch deep and are covered with topsoil. The seeds for the post-emergence test are planted two weeks prior to the seeds for the pre-emergence test, and the plants are sprayed on the same day the seeds for the pre-emergence test are planted. The amount of test compound applied is equivalent to 10 pounds per acre. The trays containing the seeds and plants are then placed in a greenhouse and the condition of the plants is observed and recorded 14 or 21 days later, depending upon the season of the year. The rating system employs a numerical scale from 0 (no damage) to 10 (plant killed). Any deformities such as stunting and leaf curl were also noted and are indicated by an appropriate letter in the accompanying table. Untreated controls were employed in both the pre-emergence (pre) and post-emergence (post) tests.

Table 1

Phytotoxicity of $(XCH_2)_2\overset{\overset{O}{\|}}{P}R$ Against Grasses

| | | Test Plants | | | | | | | | | | |
|---|---|---|---|---|---|---|---|---|---|---|---|---|
| | | Foxtail Millet *Setaria italica* (L.) Beauv. | | | | Japanese Millet *Echinochola crusgalli* (L.) Beauv. | | | | Crabgrass *Digitaria sanguinalis* (L.) Scop. | | | |
| X | R | Pre | X | Post | X | Pre | X | Post | X | Pre | X | Post | X |
| I | 4-Cl-C$_6$H$_4$ | 7$^s$ | 1 | 4 | 1 | 8$^s$ | 0 | 5$^s$ | 1 | 8$^s$ | 0 | 5$^s$ | 1 |
| I | 4-F-C$_6$H$_4$ | 8$^{s+}$ | 0 | 5$^s$ | 0 | 9$^s$ | 0 | 6$^{s+}$ | 0 | 4$^{s+}$ | 0 | 6$^s$ | 0 |
| I | naphthyl | 4$^s$ | 0 | 2 | 0 | 8$^{s,lc}$ | 0 | 2$^s$ | 0 | 6$^s$ | 0 | 2 | 0 |
| I | 4-OCH$_3$-C$_6$H$_4$ | 5$^s$ | 0 | 2 | 0 | 9$^{lc}$ | 0 | 3$^{s,lc}$ | 0 | 3$^s$ | 0 | 4$^s$ | 0 |
| I | 2-Cl-C$_6$H$_4$ | 7$^{s+}$ | 0 | 5$^s$ | 0 | 8$^{s+}$ | 0 | 7$^s$ | 0 | 2 | 0 | 3$^s$ | 0 |
| Br | 4-Cl-C$_6$H$_4$ | 5$^{s+}$ | 0 | 2$^s$ | 0 | 6$^s$ | 0 | 5$^{s+}$ | 0 | 2$^s$ | 0 | 7$^{s+}$ | 0 |
| I | 4-C$_2$H$_5$-C$_6$H$_4$ | 5$^s$ | 0 | 3 | 0 | 8$^s$ | 1 | 3 | 0 | 7$^s$ | 0 | 4$^s$ | 0 |
| Br | 4-CH$_3$-C$_6$H$_4$ | 4$^s$ | 0 | 4$^s$ | 0 | 9$^s$ | 0 | 4$^{s+}$ | 1 | 4$^s$ | 0 | 5$^s$ | 0 |
| I | N(CH$_2$—CH=CH$_2$)$_2$ | 5$^s$ | 0 | 3 | 0 | 6$^s$ | 1 | 3 | 0 | 5$^s$ | 0 | 3 | 0 |
| Br | 2-CH$_3$-C$_6$H$_4$ | 4$^s$ | 0 | 4$^s$ | 2 | 8$^s$ | 0 | 4$^s$ | 1 | 3$^s$ | 0 | 5$^s$ | 0 |
| Br | 4-OC$_2$H$_5$-C$_6$H$_4$ | 7$^{s+}$ | 0 | 3$^s$ | 0 | 7$^{s+}$ | 0 | 4$^s$ | 0 | 6$^s$ | 3 | 4$^s$ | 0 |
| I | 4-OC$_2$H$_5$-C$_6$H$_4$ | 3$^{s,lc}$ | 0 | 1 | 0 | 5$^{s,lc}$ | 1 | 1 | 0 | 4$^{s,lc}$ | 1 | 9 | 0 |
| Br | 4-F-C$_6$H$_4$ | 3$^s$ | 1 | 4$^s$ | 0 | 3$^s$ | 0 | 4$^s$ | 0 | 2$^s$ | 0 | 4$^s$ | 0 |

Table 1-continued

Phytotoxicity of $(XCH_2)_2\overset{\overset{O}{\|}}{P}R$ Against Grasses

| | | Test Plants | | | | | | | | | |
|---|---|---|---|---|---|---|---|---|---|---|---|
| | | Foxtail Millet *Setaria italica* (L.) Beauv. | | | | Japanese Millet *Echinochola crusgalli* (L.) Beauv. | | | | Crabgrass *Digitaria sanguinalis* (L.) Scop. | |
| X | R | Pre | X | Post | X | Pre | X | Post | X | Pre | X | Post | X |
| I | –C₆H₄–CF | $4^s$ | 0 | 0 | 0 | $5^s$ | 0 | 1 | 0 | $4^s$ | 0 | 1 | 0 |
| I | n-C₄H₉ | 1 | 0 | 2 | 0 | $4^{s,lc}$ | 0 | 3 | 0 | 1 | 0 | 2 | 0 |
| Control Compounds | | | | | | | | | | | | | |
| Cl | –C₆H₄–Cl | 0 | — | 0 | — | 0 | — | 1 | — | 0 | — | 1 | — |
| Cl | –C₆H₄–OCH₃ | 0 | — | 0 | — | 0 | — | 0 | — | 0 | — | 0 | — |
| I | –C₆H₃(CH₃)₂ | 0 | 1 | 2 | 0 | 0 | 0 | 2 | 0 | 0 | 0 | 2 | 0 |
| I | –C₆H₃(Cl)(NO₂) | 0 | 0 | 0 | 1 | 0 | 0 | 0 | 1 | 0 | 0 | 0 | 0 |

Notes:
$^s$ = stunting;
$^{s+}$ = severe stunting;
$^{lc}$ = leaf curl;
X = untreated control;
— = no control employed.

The data in the foregoing table demonstrate the unique ability of the present toxicants to effectively control three representative types of grasses. The last four compounds in the table were employed as controls which show relatively little activity when the bromine or iodine of the halomethyl group is replaced by chlorine or when the phenyl ring contains substituents other than those set forth in the preceding specification. Surprisingly the presence of two methyl groups or a nitro group on the phenyl ring results in a significant decrease in activity relative to the present toxicants.

Four of the compounds tested were found to be moderately effective pre-emergent growth regulators for morning glory at a concentration of ten pounds per acre. The compounds were bis(iodomethyl)-p-fluorophenylphosphine oxide, N,N-diallylbis(iodomethyl)-phosphinamide, bis(iodomethyl)-p-tolylphosphine oxide, bis(iodomethyl)-m-aminophenylphosphine oxide and bis(bromomethyl)-p-tolylphosphine oxide. While most of the present compounds are not very effective against broadleaf plants, a moderate level of control can be obtained using certain substituents on the phosphorus atom.

Both the type and level of phytotoxic activity can be varied by a judicious selection of (a) the type and location of substituents on the phenyl ring and (b) the halogen atom on the halomethyl group, represented by X in the foregoing general formula. Surprisingly, compounds of the general formula XCH₂PR₂ are relatively ineffective herbicides. Using the aforementioned test method the control ratings of bis(p-chlorophenyl)iodomethylphosphine oxide on all plants were zero.

The present phytotoxic compositions contain one or more toxicants of the general formula

as defined hereinbefore, and at least one inert liquid or solid diluent or carrier. The optimum concentration of toxicant in the composition is dependent upon a number of factors, including the amount of toxicant to be applied to each acre of plants or soil, the method of application (whether large or small scale) and whether the composition is to be applied without further dilution or employed as a concentrate which is diluted with additional carrier prior to being applied to a given area. The toxicant concentration in the final composition applied to the plant is usually between 0.01 to 50% by weight, preferably from 0.1 to 10% by weight.

In addition to toxicant and carrier, the present compositions often contain one or more surfactants or other adjuvants which allow the toxicant to be more readily dispersed or dissolved in the final formulation. The adjuvants may also facilitate prompt assimilation of the composition by the plant being treated, and can include adhesive agents to improve contact between the composition and the plant or soil being treated.

Examples of suitable liquid carriers include water, hexane, benzene, 2-butanone, acetone, isopropanol, butanediol, tetrachloroethane and various mixtures of hydrocarbons that are commercially available as petroleum ether, solvent naphtha and ligroin.

Solid carriers include natural and chemically modified materials, such as china clays, bentonite, atapulgites, acidwashed bentonite, precipitated calcium phosphate, calcined magnesia and colloidal silica. The size of these materials is less than 40 mesh (Tyler series), and preferably less than 20 mesh. Alternatively, the toxicant can be combined with a realtively small amount of one or more solid carriers and a surfactant to form a wettable powder, which is subsequently diluted with water to the desired concentration. The resultant composition is readily applied as a spray or combined with irrigation water. The sprays are conventionally applied by hand to small areas. Large areas are treated using boom sprayers or airplanes.

The amount of toxicant applied to each acre of ground is dependent upon the particular plant to be modified and the stage of growth at which it is treated. For relatively nonselective pre-emergence applications the concentration of toxicant in the composition is usually from 1 to 25 pounds per acre, preferably from 1 to 10 pounds. It may be possible to obtain adequate control of grasses at concentrations of less than 1 pound per acre using the more active compounds, for example 0.1 to 1 pound per acre.

What is claimed is:

1. A method for killing or retarding the growth of undesirable plants by applying to said plants a composition consisting essentially of at least one inert carrier and a phytotoxically effective amount of an organophosphorus compound $$(XCH_2)_2 \overset{O}{\overset{\|}{P}} R$$

wherein X is bromine or iodine, R is selected from the group consisting of

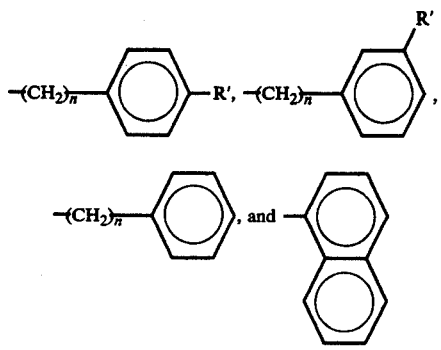

R' being in turn selected from the group consisting of $CCl_3$, $CF_3$, fluorine, chlorine, bromine, iodine, linear alkyl containing from 1 to 20 carbon atoms and linear alkoxy containing from 1 to 20 carbon atoms, R" is selected from the group consisting of unsubstituted and substituted alkyl containing from 1 to 20 carbon atoms, alkenyl containing from 2 to 4 carbon atoms and aryl, and n is 0 or 1.

2. A method according to claim 1 wherein said carrier is a liquid.
3. A method according to claim 1 wherein said composition is in the form of a wettable powder which is subsequently combined with water.
4. A method according to claim 1 wherein said carrier is a solid.
5. A method according to claim 1 wherein said plants are grasses.
6. A method according to claim 1 wherein said plants are broadleaf weeds.
7. A method according to claim 6 wherein said broadleaf weeds are morning glory.
8. A method according to claim 1 wherein said organophosphorus compound is present at a concentration of from 0.01 to 50% by weight.
9. A method according to claim 1 wherein n is 0.
10. A method according to claim 1 wherein R is

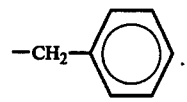

* * * * *